(12) United States Patent
Tanabe et al.

(10) Patent No.: US 7,712,959 B2
(45) Date of Patent: May 11, 2010

(54) BED FOR CAPTURING RADIATION IMAGE AND RADIATION IMAGE CAPTURING SYSTEM

(75) Inventors: Tsuyoshi Tanabe, Kanagawa (JP); Eiichi Kito, Kanagawa (JP); Takuya Yoshimi, Kanagawa (JP); Takeshi Kuwabara, Kanagawa (JP); Kazuharu Ueta, Tokyo (JP); Makoto Iriuchijima, Gunma (JP); Yasunori Ohta, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/230,135

(22) Filed: Aug. 25, 2008

(65) Prior Publication Data

US 2009/0052630 A1     Feb. 26, 2009

(30) Foreign Application Priority Data

Aug. 23, 2007   (JP)   ............................. 2007-216798
Jun. 5, 2008    (JP)   ............................. 2008-147924

(51) Int. Cl.
*H05G 1/64*   (2006.01)
*A61B 6/04*   (2006.01)

(52) U.S. Cl. ...................... 378/189; 378/98.8; 378/209; 250/370.08

(58) Field of Classification Search ................. 378/0.8, 378/189, 190, 208, 209, 98.8; 5/600, 601; 250/580–584, 370.01, 370.08, 370.09, 371
See application file for complete search history.

(56) References Cited

U.S. PATENT DOCUMENTS

| 5,877,501 | A  | * | 3/1999  | Ivan et al. ............... 250/370.09 |
| 7,126,129 | B2 |   | 10/2006 | Yamamoto |
| 7,341,375 | B2 | * | 3/2008  | Zaiki ........................... 378/196 |
| 7,426,261 | B2 | * | 9/2008  | Spahn ......................... 378/98.8 |
| 7,429,737 | B2 | * | 9/2008  | Wojcik et al. ........... 250/370.09 |
| 2002/0017610 | A1 | * | 2/2002  | Takemoto .............. 250/370.09 |
| 2002/0150214 | A1 | * | 10/2002 | Spahn ......................... 378/189 |
| 2002/0186813 | A1 | * | 12/2002 | Tamura et al. ............. 378/98.8 |
| 2004/0114725 | A1 | * | 6/2004  | Yamamoto .................. 378/189 |
| 2009/0014659 | A1 | * | 1/2009  | Hennessy et al. ....... 250/370.09 |

FOREIGN PATENT DOCUMENTS

| JP | 07-140255   | 6/1995 |
| JP | 2000-105297 | 4/2000 |
| JP | 2003-010175 | 1/2003 |
| JP | 2004-173907 | 6/2004 |

* cited by examiner

*Primary Examiner*—Edward J Glick
*Assistant Examiner*—Anastasia Midkiff
(74) *Attorney, Agent, or Firm*—Jean C. Edwards, Esq.; Akerman Senterfitt

(57) ABSTRACT

A radiation detecting cassette is disposed in a desired position between a bed and a patient in an operating room. After a detector-side connector and a bed-side connector are connected to each other by a cable, an image capturing apparatus captures and records radiation image information of the patient in a radiation detector. The recorded radiation image information is transmitted from a transceiver of the bed to a console by way of wireless communications, then processed by the console, and transmitted to a display device, which displays a radiation image based on the supplied radiation image information.

12 Claims, 8 Drawing Sheets

BED FOR CAPTURING RADIATION IMAGE AND RADIATION IMAGE CAPTURING SYSTEM

CROSS-REFERENCE TO RELATED APPLICATIONS

The present application claims priority from Japanese Patent Application Nos. 2007-216798 filed Aug. 23, 2007, and 2008-147924 filed Jun. 5, 2008, the contents of both of which are herein incorporated by reference in their entirety.

BACKGROUND OF THE INVENTION

1. Field of the Invention

The present invention relates to a bed for capturing a radiation image which is to be connected to a radiation detector, and a radiation image capturing system including such a bed.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation, or the stimulable phosphor panel is supplied to a reading device to read the radiation image as a visible image.

In the operating room or the like, it is necessary to read and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read a detected radiation image.

For capturing a radiation image with a radiation detector and transmitting information of the captured radiation image from the radiation detector to an external device, it is necessary to interconnect the radiation detector and the external device with a cable.

If the cable is connected to the radiation detector, then the cable may possibly present itself as an obstacle to the surgeons and assistants who are working in an operating room or the like that is equipped with many devices and instruments. When the cable has a portion entering the image detecting range of the radiation detector, the portion of the cable is also imaged in the radiation image captured in the radiation detector. As a result, a new radiation image free of the cable image has to be captured again.

If the radiation detector has no cable for performing communications and supplying electric power and transmits data by way of wireless communications, then the radiation detector needs to have a memory for temporarily storing the data and a battery for supplying electric power to various parts of the radiation detector, and hence is increased in size and weight.

Japanese Laid-Open Patent Publication No. 2003-010175 discloses a bed for capturing a radiation image, the bed having a gripper for gripping a cable connected to an electronic cassette which houses a radiation detector therein. When the cable is gripped by the gripper, the cable is prevented from being positioned over the electronic cassette and presenting itself as an obstacle to surgeons and other staff members working along the bed. The bed also has a controller and a power supply for the electronic cassette.

Japanese Laid-Open Patent Publication No. 2004-173907 reveals a method whereby the length of a cable connected to an electronic cassette which houses a radiation detector therein is optimized based on the distance between a connector mounted on a bed and the electronic cassette, the shoulder width of the subject, etc., and a wireless communication module is connected to the distal end of the cable for sending and receiving signals by way of wireless communications between the electronic cassette and an external device.

According to Japanese Laid-Open Patent Publication No. 2003-010175, however, since the bed and an external device are connected to each other by the cable, the surgeons and other staff members who move around the bed have to be fully aware of the existence of the cable.

According to Japanese Laid-Open Patent Publication No. 2004-173907, a battery as a source for supplying electric power for transmitting and receiving data needs to be installed in the radiation detector for transmitting and receiving data through the wireless communication module that is connected to the distal end of the cable. However, the battery makes the radiation detector relatively large in size and weight. Another problem is that when the battery installed in the radiation detector is to be charged, the wireless communication module has to be disconnected from the distal end of the cable, and a battery charger has to be connected to the distal end of the cable.

SUMMARY OF THE INVENTION

It is a general object of the present invention to provide a bed for capturing a radiation image and a radiation image capturing system which are capable of constructing a good working environment and of acquiring high-quality radiation image information.

A major object of the present invention is to provide a bed for capturing a radiation image and a radiation image capturing system which make it possible to eliminate a cable between the bed and an external device.

Another object of the present invention is to provide a bed for capturing a radiation image and a radiation image capturing system which are capable of transmitting radiation image information from a radiation detector to the bed in a state that is less susceptible noise.

Still another object of the present invention is to provide a bed for capturing a radiation image and a radiation image capturing system which allow a radiation detector to be reduced in size and weight with ease.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
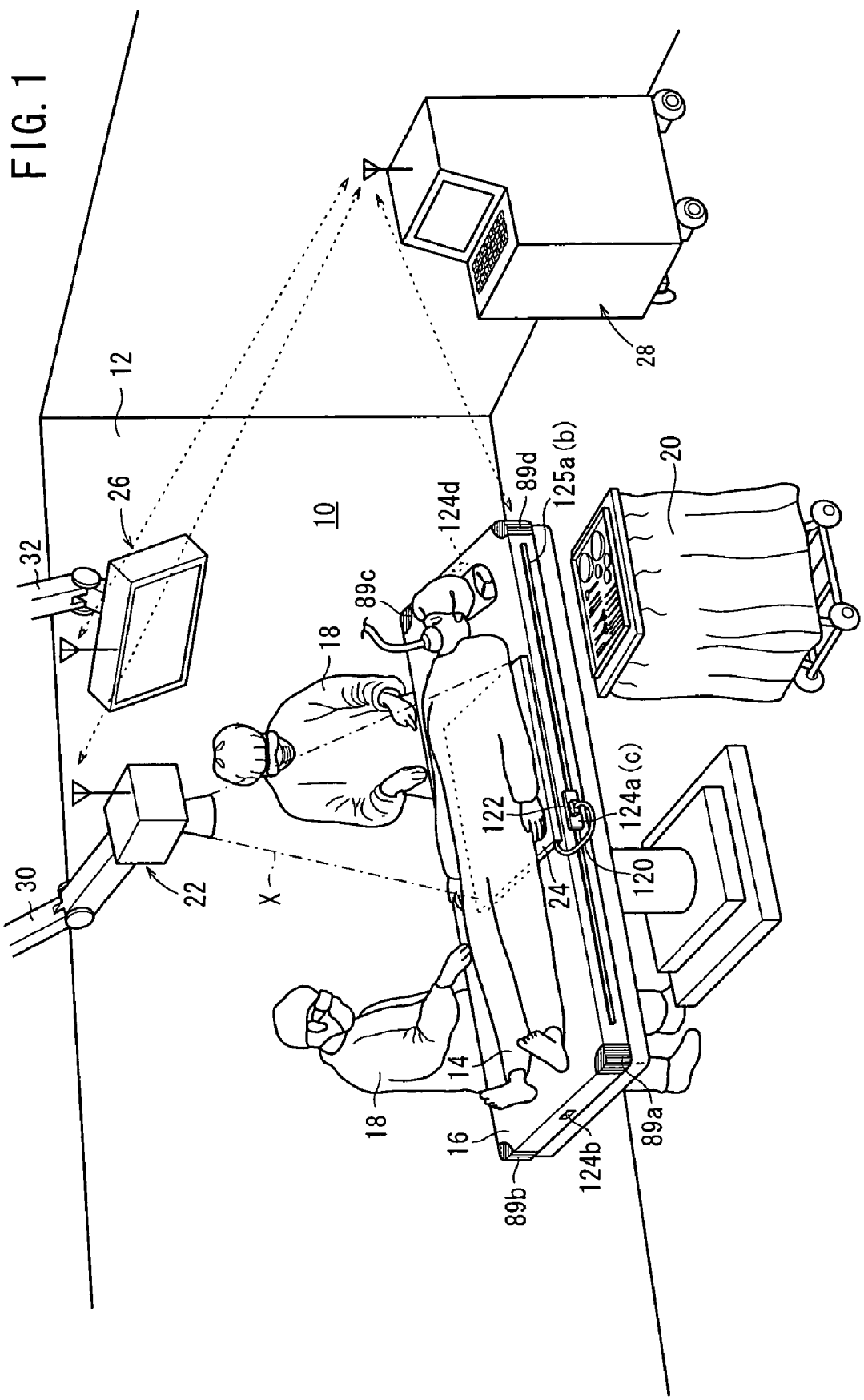
FIG. 1 is a perspective view of an operating room incorporating a radiation image capturing system according to an embodiment of the present invention.

FIG. 1 shows in perspective an operating room 12 incorporating a radiation image capturing system 10 according to an embodiment of the present invention.

As shown in FIG. 1, the operating room 12 has, in addition to the radiation image capturing system 10, a bed 16 for capturing a radiation image, and an instrument table 20 disposed on one side of the bed 16 for placing thereon various tools and instruments to be used by surgeons 18 for operating a patient 14 lying on the bed 16. The bed 16 is surrounded by various apparatus required for surgical operations, including an anesthesia apparatus, an aspirator, an electrocardiograph, a blood pressure monitor, etc.

The radiation image capturing system 10 includes an image capturing apparatus 22 for irradiating the patient 14 with a radiation X at a dose according to image capturing conditions, a radiation detecting cassette 24 housing therein a radiation detector, to be described later, for detecting the radiation X that has passed through the patient 14, the bed 16 to which the radiation detecting cassette 24 is connected, a display device 26 for displaying a radiation image based on the radiation X that is detected by the radiation detector, and a console (processor) 28 for controlling the image capturing apparatus 22, the radiation detecting cassette 24, and the display device 26.

The radiation detecting cassette 24 and the bed 16 send and receive signals by way of wired communications, and the bed 16, the image capturing apparatus 22, the display device 26, and the console 28 send and receive signals by way of wireless communications.

The image capturing apparatus 22 is coupled to a universal arm 30 so as to be movable to a desired position for capturing a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 2:
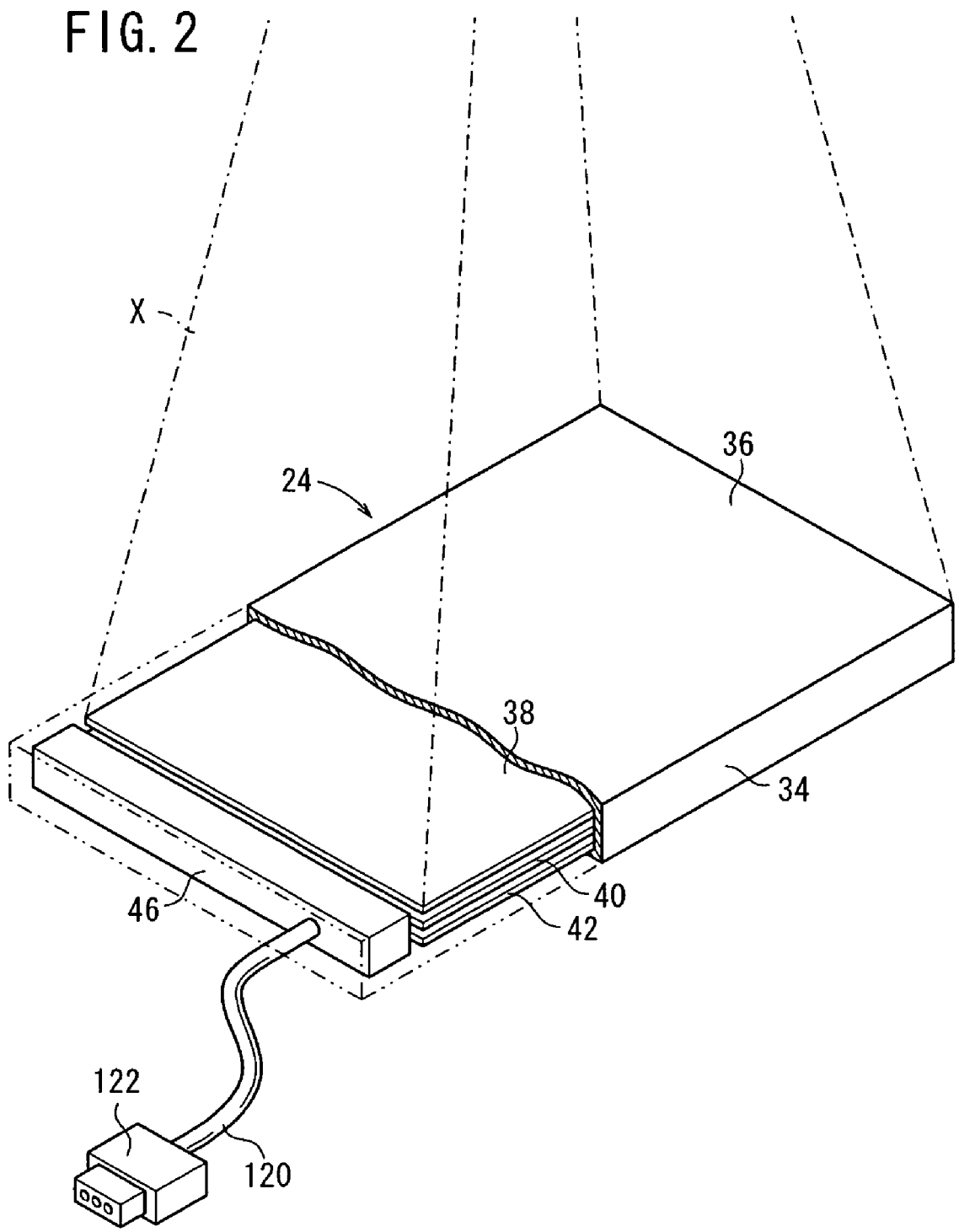
FIG. 2 is a perspective view, partly cut away, showing internal structural details of a radiation detecting cassette used in the radiation image capturing system.

FIG. 2 shows internal structural details of the radiation detecting cassette 24. As shown in FIG. 2, the radiation detecting cassette 24 has a casing 34 made of a material permeable to the radiation X. The casing 34 houses therein a grid 38 for removing scattered rays of the radiation X from the patient 14, a radiation detector 40 for detecting the radiation X that has passed through the patient 14, and a lead plate 42 for absorbing back scattered rays of the radiation X, which are successively arranged in that order from a surface 36 of the casing 34 which is irradiated with the radiation X. The irradiated surface 36 of the casing 34 may be constructed as the grid 38.

The casing 34 also houses therein a cassette controller 46 for energizing the radiation detector 40. A detector-side connector 122 for connecting the radiation detector 40 to an external device is connected to the cassette controller 46 by a cable 120. The cassette controller 46 is supplied with electric power from the external device through the detector-side connector 122 and the cable 120, and sends and receives signals representative of radiation image information detected by the radiation detector 40. A shield plate of lead or the like should preferably be placed between the irradiated surface 36 of the casing 34 and the cassette controller 46 to protect the cassette controller 46 against damage which would otherwise be caused if irradiated with the radiation X.

Figure 3:
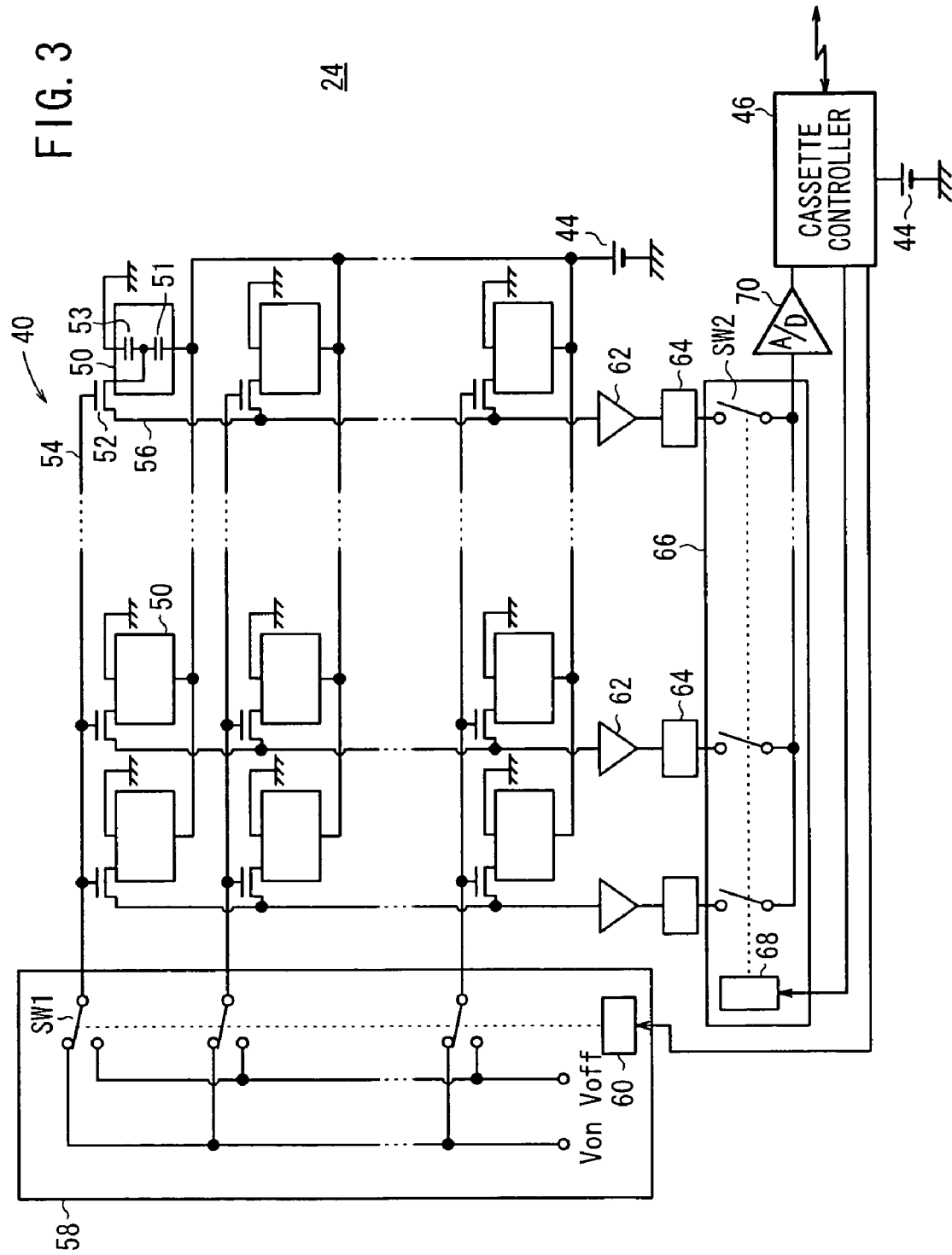
FIG. 3 is a block diagram of a circuit arrangement of a radiation detector.

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed on the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used in a certain temperature range. Therefore, some means for cooling the radiation detector 40 should preferably be provided in the radiation detecting cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 4:
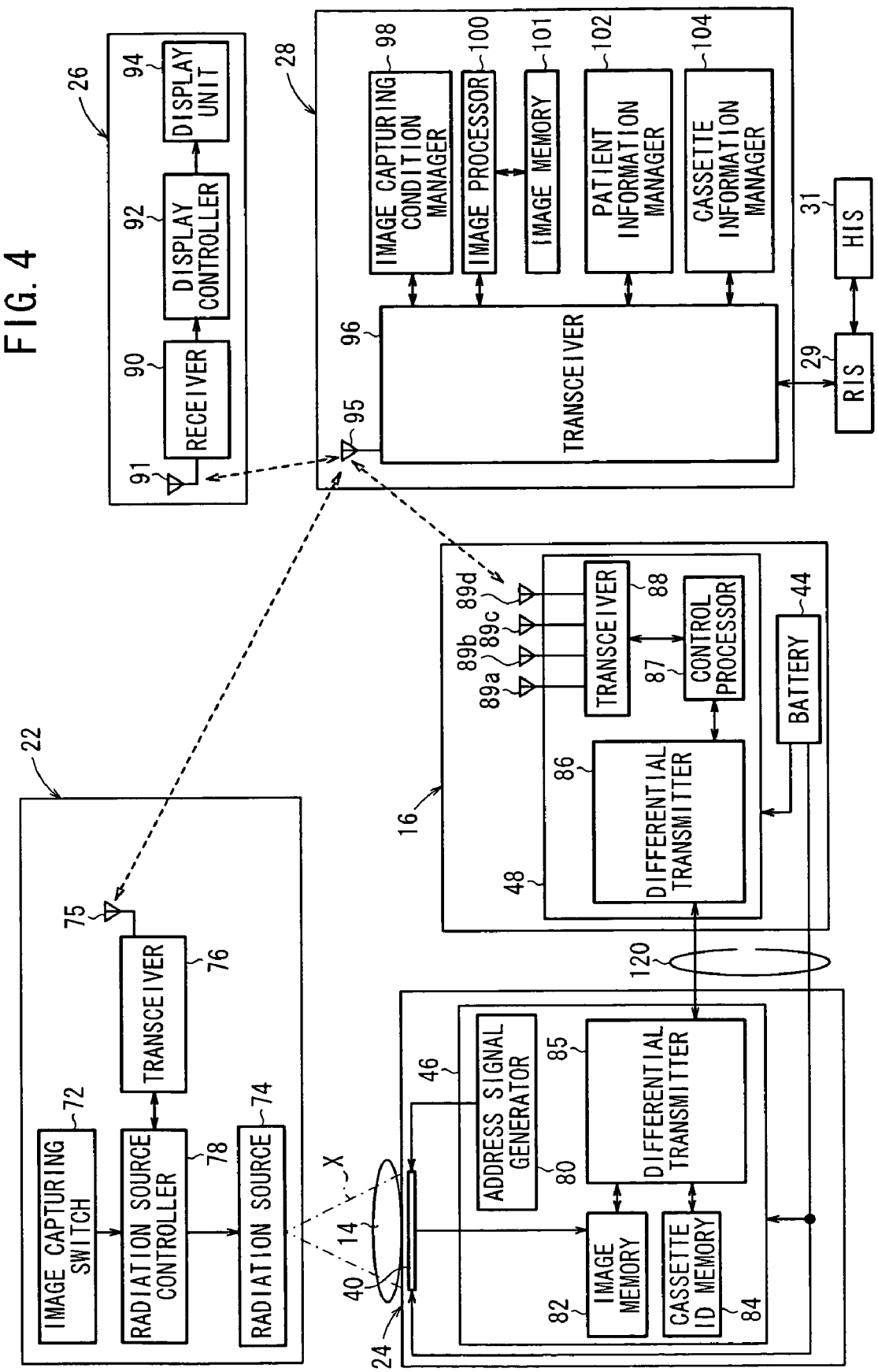
FIG. 4 is a block diagram of the radiation image capturing system.

FIG. 4 shows in block form the radiation image capturing system 10 which comprises the bed 16, the image capturing apparatus 22, the radiation detecting cassette 24, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 72, a radiation source 74 for outputting the radiation X, a transceiver 76 for receiving image capturing conditions from the console 28 via an antenna 75 by way of wireless communications and transmitting an image capturing completion signal, etc. to the console 28 via the antenna 75 by way of wireless communications, and a radiation source controller 78 for controlling the radiation source 74 based on an image capturing start signal supplied from the image capturing switch 72 and image capturing conditions supplied from the transceiver 76.

The cassette controller 46 which is housed in the radiation detecting cassette 24 comprises an address signal generator 80 for supplying address signals to the address decoder 60 of the line scanning driver 58 and the address decoder 68 of the multiplexer 66 of the radiation detector 40, an image memory 82 for storing the radiation image information detected by the radiation detector 40, a cassette ID memory 84 for storing cassette ID information for identifying the radiation detecting cassette 24, and a differential transmitter 85. The differential transmitter 85 transmits and receives data to the bed 16 via a cable 120 by way of wired communications.

The bed 16 houses therein a battery 44 and a transmission and reception processor 48. The transmission and reception processor 48 comprises a differential transmitter (communicating unit) 86 for transmitting and receiving data to and from the differential transmitter 85 of the radiation detecting cassette 24 via the cable 120 by way of wired communications, a transceiver 88, a plurality of antennas 89*a* through 89*d* serving as wireless communication units, and a control processor 87.

Figure 5:
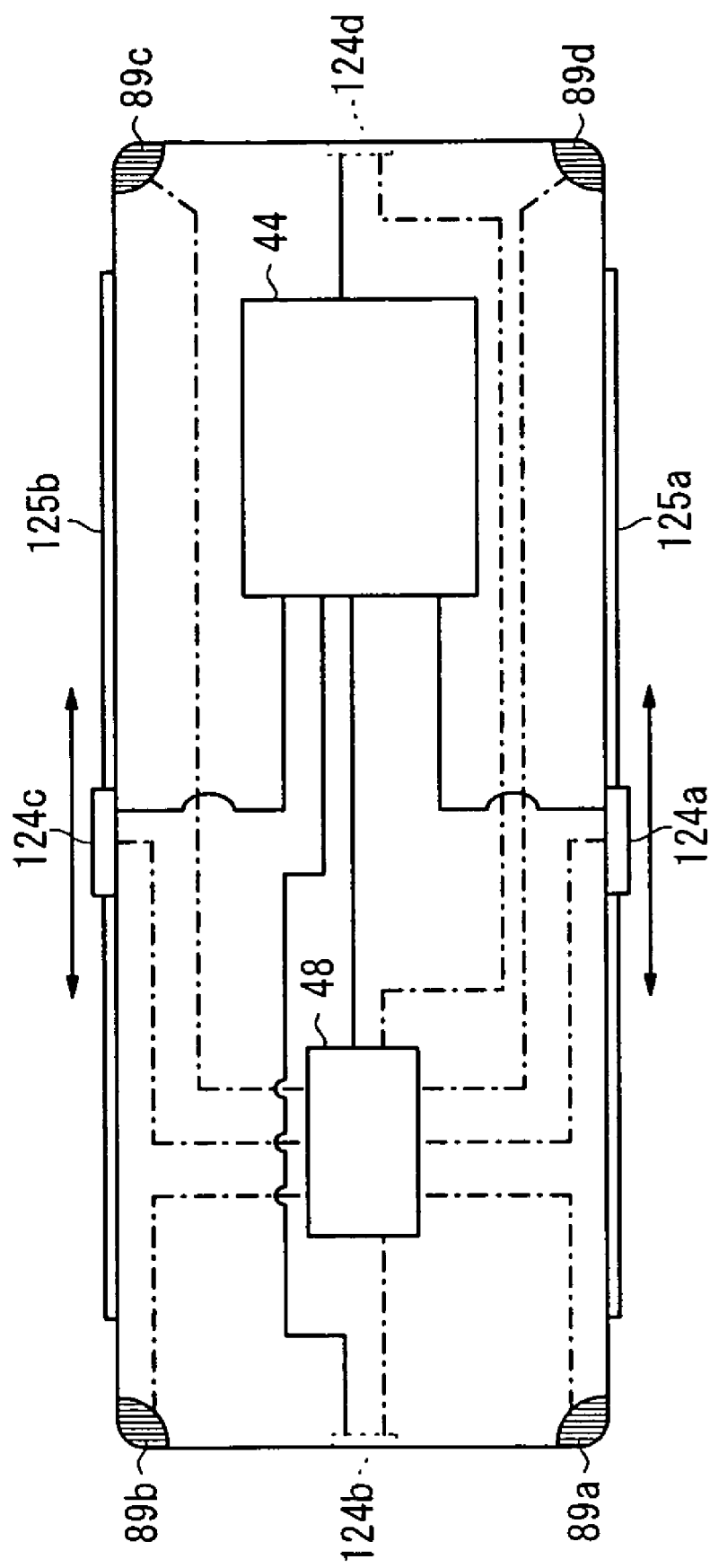
FIG. 5 is a plan view of a bed for capturing a radiation image which is incorporated in the radiation image capturing system.
Figure 6:
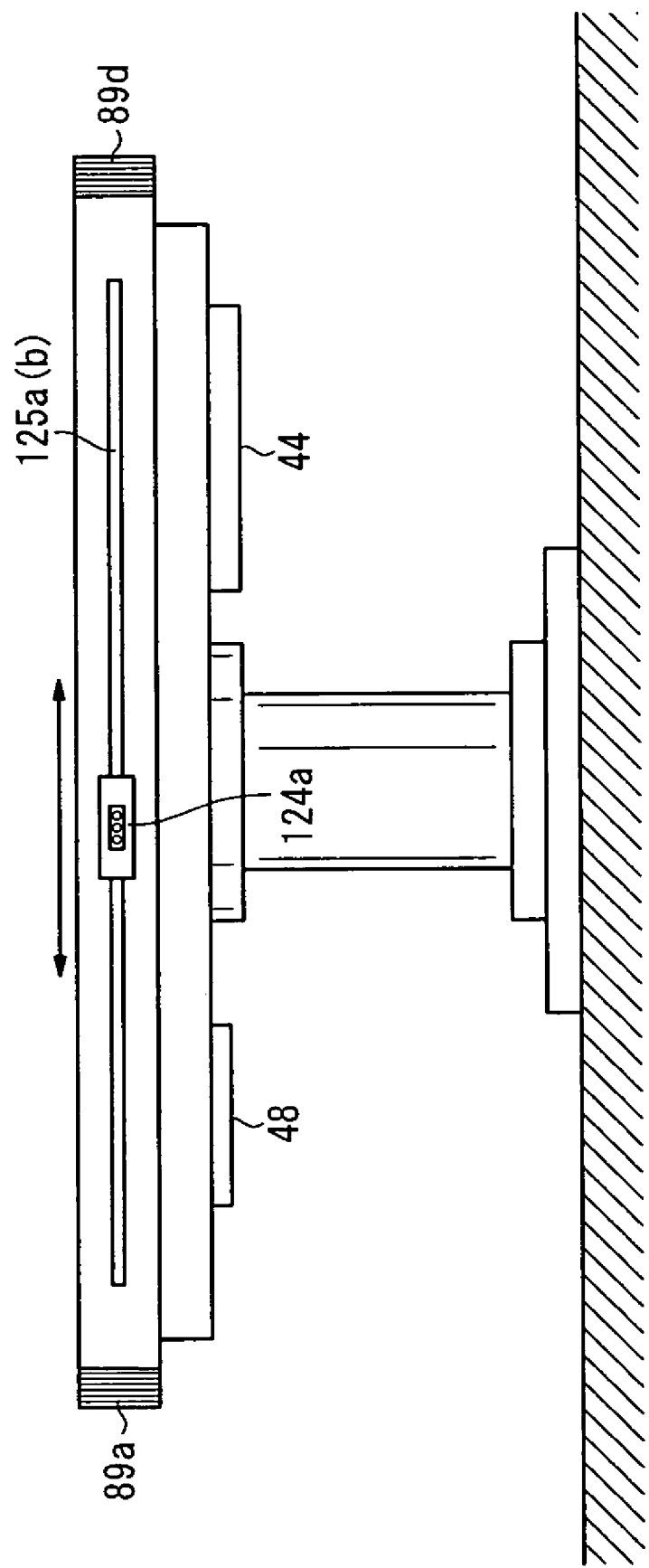
FIG. 6 is a side elevational view of the bed for capturing a radiation image.

As shown in FIGS. 5 and 6, the detector-side connector 122 on the cable 120 of the radiation detecting cassette 24 can be connected to any one of bed-side connectors 124*a* through 124*d* that are disposed on respective sides of the bed 16. Specifically, the bed-side connectors 124*a*, 124*c* are disposed on respective longitudinal sides of the bed 16 and movable in the directions indicated by the arrows along respective guide rails 125*a*, 125*b* on the longitudinal sides of the bed 16. When the radiation detecting cassette 24 is placed in a predetermined position on the bed 16, the cable 120 can connect the radiation detecting cassette 24 to the closest one of the bed-side connectors 124*a* through 124*d*. Therefore, the cable 120 has a minimum length required to connect the radiation detecting cassette 24 placed on the bed 16 to either one of the bed-side connectors 124*a* through 124*d* according to the positional relationship between the radiation detecting cassette 24 placed on the bed 16 and the bed-side connectors 124*a* through 124*d*.

The antennas 89*a* through 89*d* are disposed in the respective corners of the bed 16 which are less likely to be shielded by the surgeons 18, other staff members, and various devices and instruments in the operating room 12.

The transmission and reception processor 48 of the bed 16 receives a transmission request signal from the console 28 via the antennas 89*a* through 89*d* and transmits the transmission request signal to the radiation detecting cassette 24 via the cable 120. The transmission and reception processor 48 also receives the cassette ID information stored in the cassette ID memory 84 and the radiation image information stored in the image memory 82, and transmits the cassette ID information and the radiation image information to the console 28 from the antennas 89*a* through 89*d* by way of wireless communications. The control processor 87 has a function to compress radiation image information. Since the amount of data of the radiation image information is large, the control processor 87 compresses the radiation image information to reduce the amount of data thereof that is to be transmitted. The reduced amount of data can be transmitted in a shortened transmission time and at a reduced transmission rate by way of wireless communications.

The battery 44 housed in the bed 16 supplies electric power to the transmission and reception processor 48 and the radiation detecting cassette 24. The radiation detecting cassette 24 is supplied with the electric power from the battery 44 via the cable 120.

The display device 26 comprises a receiver 90 for receiving radiation image information from the console 28 via an antenna 91, a display controller 92 for controlling the display of the received radiation image information, and a display unit 94 for displaying the radiation image information processed by the display controller 92.

The console 28 comprises a transceiver 96 for transmitting and receiving necessary information including radiation image information to and from the image capturing apparatus 22, the bed 16, and the display device 26 via an antenna 95 by way of wireless communications, an image capturing condition manager 98 for managing image capturing conditions required for the image capturing apparatus 22 to capture radiation images, an image processor 100 for processing radiation image information transmitted from the bed 16, an image memory 101 for storing the radiation image information processed by the image processor 100, and a patient information manager 102 for managing patient information of the patient 14 whose images are to be captured. The console 28 may be located outside of the operating room 12 insofar as it can transmit and receive signals to and from the image capturing apparatus 22, the bed 16, and the display device 26 by way of wireless communications.

The image capturing conditions refer to condition for determining a tube voltage, a tube current, an irradiation time, etc. required to apply a radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for instructing the radiation image capturing system 10 to capture a radiation image, including the image capturing conditions and the patient information, can be set directly on the console 28 or can be supplied from an external source to the console 28 via the RIS 29. A cassette information manager 104 manages cassette ID information or the like for identifying the radiation detecting cassette 24.

The radiation image capturing system 10 according to the present embodiment is basically constructed as described above, and operation of the radiation image capturing system 10 will be described below.

The radiation image capturing system 10 is installed in the operating room 12 and used when a radiation image of the patient 14 is required by the surgeons 18 who are performing an operation on the patient 14. Before a radiation image of the patient 14 is captured, patient information of the patient 14 to be imaged is registered in the patient information manager 102 of the console 28. If an area to be imaged of the patient 14 and an image capturing method have already been known, they are registered as image capturing conditions in the image capturing condition manager 98. After the above preparatory process is finished, the surgeons 18 perform an operation on the patient 14.

For capturing a radiation image of the patient 14 during the operation, one of the surgeons 18 or the radiological technician places the radiation detecting cassette 24 in a given position between the patient 14 and the bed 16 with the irradiated surface 36 facing the image capturing apparatus 22. Thereafter, the detector-side connector 122 on the cable 120 of the radiation detecting cassette 24 is connected to the closest one of the bed-side connectors 124a through 124d. At this time, the bed-side connector 124a or 124c may be moved along the guide rail 125a or 125b on the longitudinal side of the bed 16 before the cable 120 is connected.

Based on the relationship between the position of the radiation detecting cassette 24, the positions of the bed-side connectors 124a through 124d, and the height of the bed 16 from the floor, the length of the cable 120 is set to a minimum required to connect the cable 120 to any one of the bed-side connectors 124a through 124d, thereby preventing the cable 120 from hanging into contact with the floor and picking up dust or the like before the cable 120 is connected to any one of the bed-side connectors 124a through 124d. Preferably, the length of the cable 120 should be smaller than the height of the bed 16 so that the cable 120 will not contact the floor no matter where the radiation detecting cassette 24 may be placed on the bed 16. The minimum required length of the cable 120 is highly effective from a sanitary viewpoint in the operating room 12. The minimum required length of the cable 120 is also effective in minimizing electromagnetic disturbances which the cable 120 suffers and acquiring radiation image information of good quality.

Figure 7:
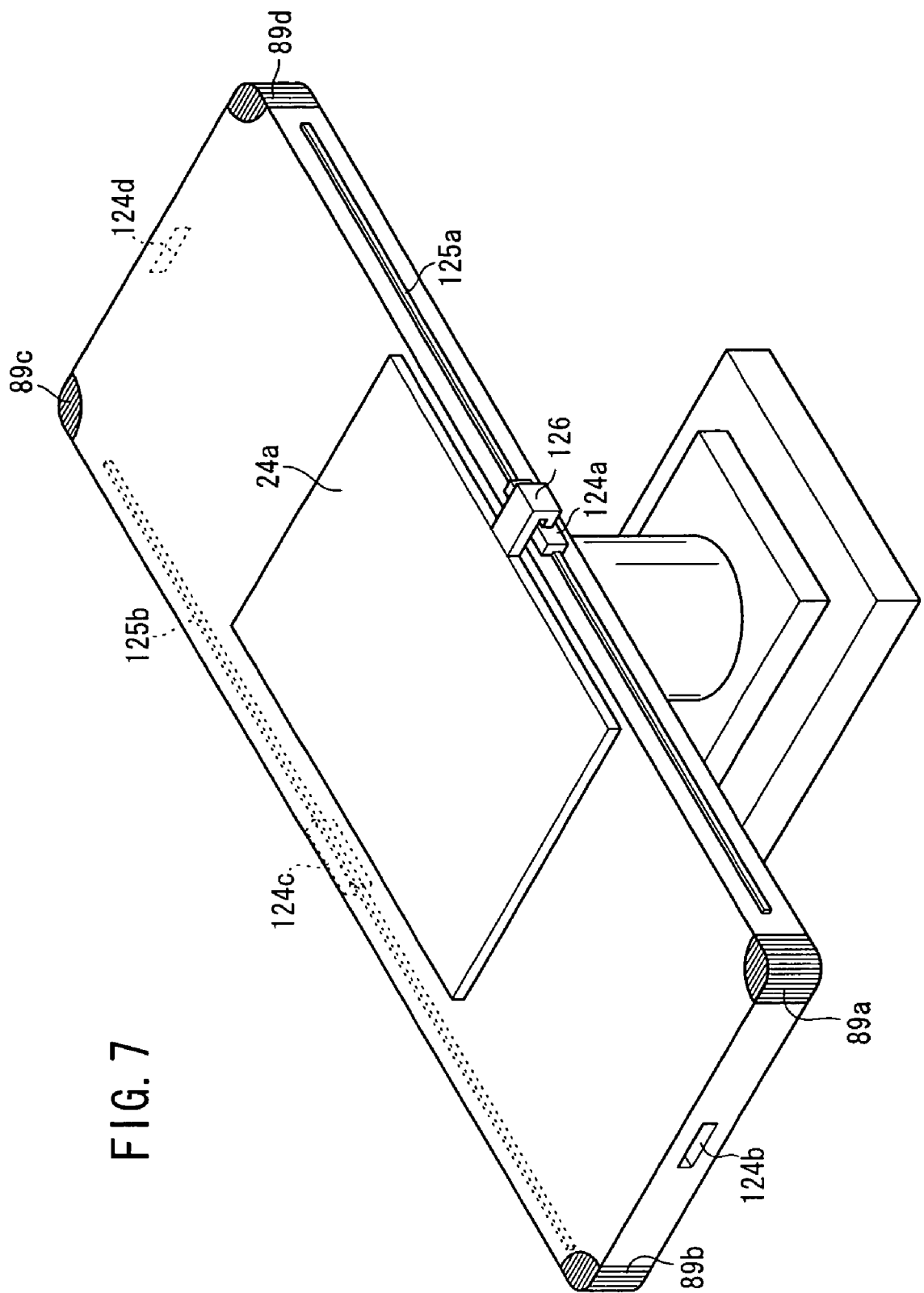
FIG. 7 is a perspective view of the bed to which another radiation detecting cassette is connected.

FIG. 7 shows another radiation detecting cassette 24a which is free of the cable 12. The radiation detecting cassette 24a is connected to the bed-side connector 124a of the four bed-side connectors 124a through 124d of the bed 16. The radiation detecting cassette 24a has a detector-side connector 126 directly mounted on a side thereof. The detector-side connector 126 is connected to the bed-side connector 124a that is positioned most closely to the detector-side connector 126, thereby connecting the radiation detecting cassette 24a to the bed 16. The radiation detecting cassette 24a may be connected to one of the other bed-side connectors 124b through 124d which is selected depending on where the radiation detecting cassette 24a is placed on the bed 16.

Then, after having moved the image capturing apparatus 22 to a position confronting the radiation detecting cassette 24, one of the surgeons 18 or the radiological technician turns on the image capturing switch 72 to capture a radiation image of the patient 14.

The radiation source controller 78 of the image capturing apparatus 22 acquires image capturing conditions about the area to be imaged of the patient 14 from the image capturing condition manager 98 of the console 28 via the transceivers 96, 76 by way of wireless communications. When the radiation source controller 78 receives the image capturing conditions, it controls the radiation source 74 to apply a radiation X at a given dose to the patient 14 according to the acquired image capturing conditions.

The radiation X which has passed through the patient 14 is applied to the grid 38, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges, which represent radiation image information of the patient 14, are read from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading the electric charges stored in the storage capacitors 53 of the pixels 50 connected to the selected gate line 54, through the signal lines 56.

The electric charges read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges stored in the storage capacitors 53 of the pixels 50 connected to the successively selected gate lines 54 are read through the signal lines 56, and processed by the multiplexer 66 and the A/D converter 70 into digital signals, which are stored in the image memory 82 of the cassette controller 46.

The radiation image information of the patient 14 represented by the digital signals stored in the image memory 82 is transmitted, together with the cassette ID information stored in the cassette ID memory 84, via the cable 120 to the differential transmitter 86 of the bed 16. Signals may alternatively be transmitted between the radiation detecting cassette 24 and the bed 16 through any of other transmission mediums than the differential transmitters 85, 86 and the cable 120.

When the control processor 87 receives the radiation image information and the cassette ID information from the differential transmitter 86, the control processor 87 compresses the radiation image information, and transmits the compressed radiation image information and the cassette ID information from the transceiver 88 through the antennas 89a through 89d to the console 28. Details of the transmission from the bed 16 to the console 28 will be described later.

The radiation image information and the cassette ID information transmitted to the console 28 are received by the transceiver 96, processed by the image processor 100 to expand the compressed radiation image information, for example, and then stored in the image memory 101 in association with the patient information of the patient 14 registered in the patient information manager 102.

The radiation image information processed by the image processor 100 is transmitted from the transceiver 96 to the display device 26. In the display device 26, the receiver 90 receives the radiation image information, and the display controller 92 controls the display unit 94 to display a radiation image based on the radiation image information. The surgeons 18 perform the operation on the patient 14 while visually confirming the radiation image displayed on the display unit 94.

Since no cables for transmitting and receiving signals are connected between the bed 16 with the radiation detecting cassette 24 connected thereto and the console 28, between the image capturing apparatus 22 and the console 28, and between the console 28 and the display device 26, no such cables are placed on the floor of the operating room 12 and hence there are no cable-induced obstacles to the operation performed by the surgeons 18, the radiological technician, or other staff members in the operating room 12.

A process of sending and receiving signals between the transmission and reception processor 48 of the bed 16 and the console 28 will be described below.

A radiation image is captured of the patient 14 while the surgeons 18, the staff members or assistants, and the radiological technician (hereinafter generally referred to as "attendant") are present around the bed 16. As the surgical operation on the patient 14 goes on, the area of the patient 14 which is being operated varies and also the details of the surgical operation vary, so that the standing positions of the attendants vary dynamically.

In surgical operations accompanied by the capturing of radiation images, the attendants wear a radiation protection suit combined with a lead shield for protection against exposure to the radiation. The radiation protection suit serves to protect the human body against the radiation and also serves as a shield in wireless communications. When the standing position of an attendant varies dynamically, the attendant may move across a path of wireless communications, interrupting the wireless communications, or may move to and stop on a path of wireless communications, blocking the wireless communications. Such obstacles caused by attendants wearing radiation protection suits should be taken into account in providing smooth wireless communications.

According to the present embodiment, the bed 16 has the plural antennas 89a through 89d, and the transceiver 88 includes a selector, not shown, for selecting the antennas 89a through 89d to solve the above problem. The antennas 89a through 89d provide respective wireless communication paths, and the selector for selecting the antennas 89a through 89d makes it possible to use an optimum one of the wireless communication paths.

Processes of selecting the antennas 89a through 89d will be described below. According to one of the selecting processes, the bed 16 selects the antennas 89a through 89d autonomously based on a signal from the console 28. Specifically, the antennas 89a through 89d receive data transmitted from the console 28. Based on the received data, the selector determines an optimum one of the antennas 89a through 89d. When the bed 16 performs wireless communications to the console 28, the selector selects one of the antennas 89a through 89d based on the determined result.

The received data from the console 28 may represent a communication BER (Bit Error Rate) between the console 28 and the bed 16 or received radio-wave intensity at the bed 16. Though an optimum communication unit may be selected from time to time, the history of communication BERs or received radio-wave intensity may be managed and a rate of change of the communication BERs or received radio-wave intensities may be taken into account.

According to another selecting process, the power reflection (S11 parameter) of an antenna is measured. Specifically, when there are a plurality of attendants in a small space such as the operating room 12, one or more of the attendants occasionally move into contact with or closely to the antennas 89a through 89d. At this time, the input impedances of the antennas 89a through 89d change due to the presence of the attendants, and the impedance matching between the antennas 89a through 89d and the transceiver 88 deviates from an appropriate value. As a result, the electric power reflected from the antennas 89a through 89d to the transceiver 88 increases, reducing the radiation of power into the space. Consequently, when the bed 16 transmits data to the console 28, the power reflections from the antennas 89a through 89d are measured. Based on the measured power reflections, one of the antennas 89a through 89d is selected, and data such as radiation image information are transmitted through the selected antenna. One of the antennas 89a through 89d to be used may be determined based on the management of the history of the power reflections from the antennas 89a through 89d.

The layout of the antennas 89a through 89d will be described below. As described above, the antennas 89a through 89d provide respective wireless communication paths. As the communication environment varies due to the standing positions of the attendants and changes in the standing positions of the attendants, at least one of the antennas 89a through 89d should desirably be positioned remotely to the extent that it will not be shielded by the attendants at all times. The console 28 and the bed 16 which communicate with each other may not necessarily be kept constantly positioned with respect to each other at all times, but their relative positional relationship usually tends to change from surgical operation to surgical operation. Accordingly, it is desirable that each of the antennas 89a through 89d should have a wide communication range. To meet such requirements, the antennas 89a through 89d are disposed in the respective corners of the bed 16 as described above. The corners of the bed 16 are less likely to be shielded by the attendants than the sides of the bed 16.

The bed 16 and the console 28 may perform wireless communications with each other through the image capturing apparatus 22 rather than directly performing wireless communications with each other. In such a case, the antennas 89a through 89d may be oriented toward the image capturing apparatus 22.

The radiation detector 40 housed in the radiation detecting cassette 24 directly converts the dose of the applied radiation X into an electric signal with the photoelectric conversion layer 51. However, the radiation image capturing system 10 may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system 10 may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

When the radiation detecting cassette 24 is used in the operating room 12 or the like, blood stains and contaminants may be applied to the radiation detecting cassette 24. The radiation detecting cassette 24 may be of a water-resistant, sealed structure so that they can be sterilized and cleaned to remove such blood stains and contaminants for repetitive use.

The radiation detecting cassette 24 is not limited to being used in the operating room 12, but may be used in combination with medical examinations and doctor's visits to patient rooms in the hospital.

Figure 8:
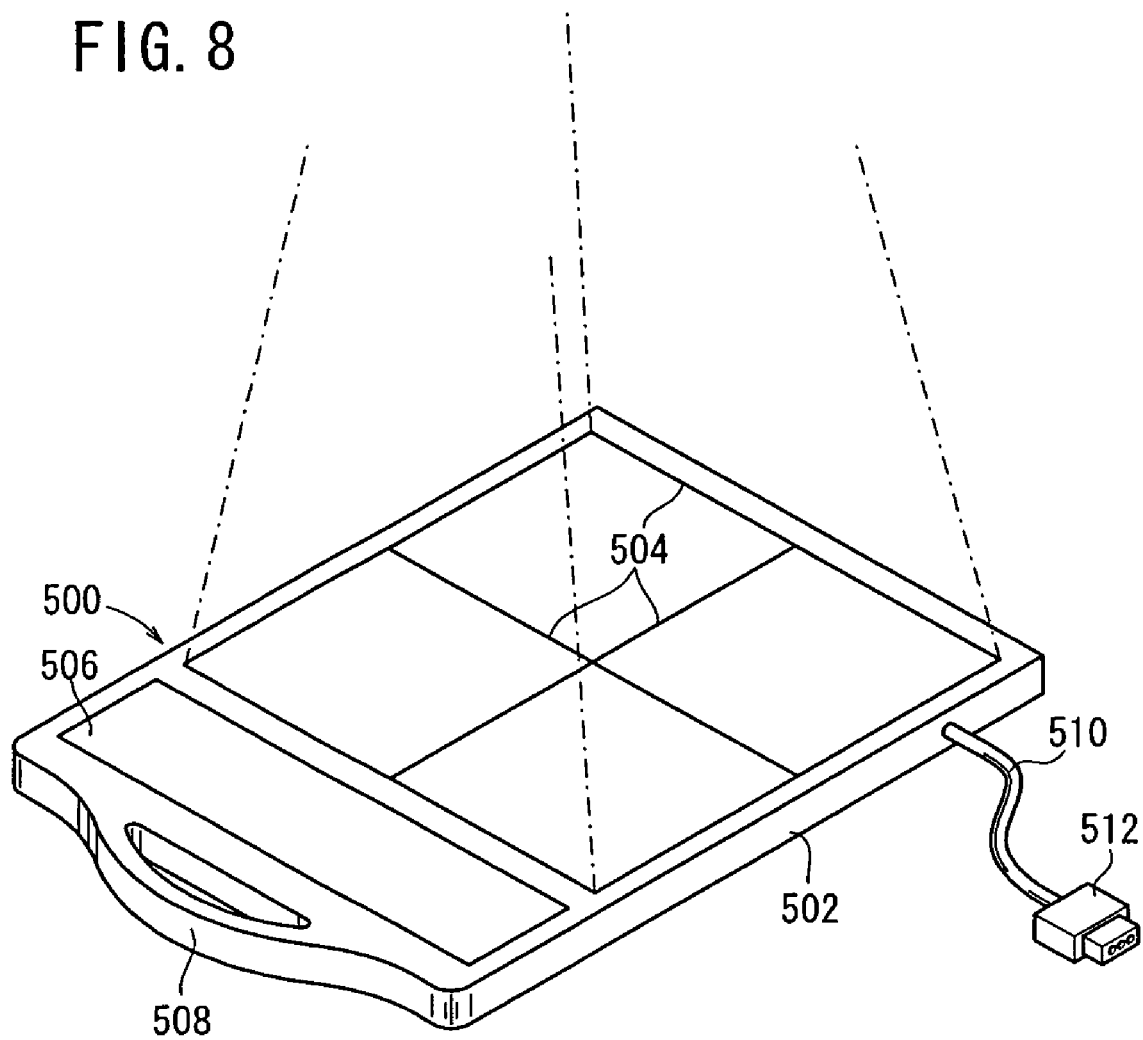
FIG. 8 is a perspective view showing still another radiation detecting cassette used in the radiation image capturing system.

FIG. 8 is a perspective view showing still another radiation detecting cassette 500 used in the radiation image capturing system.

As shown in FIG. 8, the radiation detecting cassette 500 includes a casing 502 having a side connected to a detector-side connector 512 by a cable 510. The radiation detecting cassette 500 has guide lines 504 drawn on the irradiated surface of the casing 502 as a reference mark for an image capturing area and an image capturing position. Using the guide lines 504, the subject to be imaged, such as the patient 14, can be positioned with respect to the radiation detecting cassette 500 and the range in which the radiation is to be applied to the cassette 500 can be determined, for thereby recording radiation image information in an appropriate image capturing area of the cassette 500.

The radiation detecting cassette 500 also has a display unit 506 outside of the image capturing area thereof for displaying various items of information about the radiation detecting cassette 500. Specifically, the display unit 506 displays ID information of the subject, e.g., the patient 14, whose radiation image is recorded in the radiation detecting cassette 500, the number of times that the radiation detecting cassette 500 has been used, an accumulated exposed dosage, image capturing conditions for radiation image information, and a positioning image representing the patient 14 positioned with respect to the radiation detecting cassette 500, etc. The radiological technician can confirm the patient 14 based on the ID information displayed on the display unit 506, also confirm in advance that the radiation detecting cassette 500 is in a usable state, position the desired area to be imaged of the patient 14 with respect to the radiation detecting cassette 500 based on the displayed positioning image, and capture optimum radiation image information in the radiation detecting cassette 500.

The cassette 500 includes a handle 508 to be gripped by the user to handle and carry the radiation detecting cassette 500 with ease.

Although certain preferred embodiments of the present invention have been shown and described in detail, it should be understood that various changes and modifications may be made therein without departing from the scope of the appended claims.

What is claimed is:

1. A bed for capturing a radiation image of a subject, comprising:
    a bed-side connector for being connected by a wired link to a detector-side connector of a radiation detector for detecting radiation image information of the subject;
    a communicating unit for receiving the radiation image information detected by the radiation detector through said detector-side connector and said bed-side connector which are connected to each other; and
    a wireless communicating unit for transmitting the radiation image information received by said communicating unit to an external device by way of wireless communications.

2. A bed according to claim 1, wherein said wireless communicating unit comprises a plurality of wireless communicating units, said bed further comprising:
    a selector for selecting at least one of said wireless communicating units;
    wherein said one of said wireless communicating units which is selected by said selector transmits the radiation image information to the external device.

3. A bed according to claim 1, wherein said wireless communicating unit is disposed in a corner of the bed.

4. A bed according to claim 1, wherein said bed-side connector comprises a plurality of bed-side connectors respectively in a plurality of locations on sides of the bed, and said detector-side connector is connected to a selected one of said bed-side connectors.

5. A bed according to claim 1, wherein said bed-side connector is disposed on a side of the bed and is movable along the side of the bed.

6. A bed according to claim 1, for use in an operating room.

7. A radiation image capturing system comprising:
    a radiation detector for detecting radiation image information of the subject;
    a bed for capturing a radiation image of a subject, said bed including a bed-side connector for being connected by a wired link to a detector-side connector of said radiation detector;
    a communicating unit disposed on said bed for receiving the radiation image information detected by said radiation detector through said detector-side connector and said bed-side connector which are connected to each other;
    a wireless communicating unit disposed on said bed for transmitting the radiation image information received by said communicating unit to an external device by way of wireless communications; and
    a processor, provided as said external device, for receiving and processing the radiation image information transmitted from said wireless communicating unit.

8. A radiation image capturing system according to claim 7, wherein said wireless communicating unit comprises a plurality of wireless communicating units,
    wherein said bed further comprises a selector for selecting at least one of said wireless communicating units;
    wherein said one of said wireless communicating units which is selected by said selector transmits the radiation image information to said processor.

9. A radiation image capturing system according to claim 7, wherein said wireless communicating unit is disposed in a corner of the bed.

10. A radiation image capturing system according to claim 7, wherein said bed-side connector comprises a plurality of bed-side connectors disposed respectively in a plurality of locations on sides of the bed, and said detector-side connector is connected to a selected one of said bed-side connectors.

11. A radiation image capturing system according to claim 7, wherein said bed-side connector is disposed on a side of the bed and is movable along the side of the bed.

12. A radiation image capturing system according to claim 7, wherein said bed is disposed in an operating room.

* * * * *